United States Patent [19]

Bloomfield

[11] Patent Number: 5,248,680
[45] Date of Patent: Sep. 28, 1993

US005248680A

[54] ZWITTERIONIC COMPOUNDS AND THEIR N-HALO DERIVATIVES FOR USE IN THE TREATMENT OF CLINICAL CONDITIONS

[75] Inventor: Frederick J. Bloomfield, Bellévue, Ireland

[73] Assignee: Bloomfield D.A., Oslo, Norway

[21] Appl. No.: 736,247

[22] Filed: Jul. 26, 1991

[30] Foreign Application Priority Data

Jul. 30, 1990 [iE] Ireland ................................. 2741

[51] Int. Cl.$^5$ ........................................... A61K 31/535
[52] U.S. Cl. ................... 514/238.8; 514/255; 514/553; 514/665
[58] Field of Search ................. 514/665, 238.8, 255, 514/553

[56] References Cited

U.S. PATENT DOCUMENTS

| | | |
|---|---|---|
| 4,473,569 | 9/1984 | O'Sullivan . |
| 4,544,656 | 10/1985 | O'Sullivan ........................ 514/228 |
| 4,753,942 | 6/1988 | O'Sullivan ........................ 514/255 |

FOREIGN PATENT DOCUMENTS

| | | |
|---|---|---|
| 0098073 | of 0000 | European Pat. Off. . |
| 0228239 | of 0000 | European Pat. Off. . |
| 0361908 | of 0000 | European Pat. Off. . |
| WO80/9657 | of 0000 | PCT Int'l Appl. . |

OTHER PUBLICATIONS

Milei, J. et al., (1992) Amer. Heart Jour. vol. 123, No. 2 pp. 339-345.

*Primary Examiner*—Leonard Schenkman
*Attorney, Agent, or Firm*—Felfe & Lynch

[57] ABSTRACT

Zwitterionic compounds selected from:
taurine (2-aminoethanesulphonic acid),
2(N-morpholino)ethanesulphonic acid (MES),
N-(2-acetamido)iminodiacetic acid (ADA),
piperazine-N,N'bis(2-ethanesulphonic acid (PIPES),
N-(2-acetamido)-2-aminoethanesulphonic acid (ACES),
N,N-bis(2-hydroxyethyl)-2-aminoethanesulphonic acid (BES),
3-(N-morpholino)propanesulphonic (MOPS),
N-N[tris(hydroxymethyl)-methyl]-2-aminoethanesulphonic acid (TES),
N-2-hydroxyethylpiperazine-N'-2-ethanesulphonic acid (HEPES),
N-2-hydroxyethylpiperazine-N'3-propanesulphonic acid (H)EPPS),
2-(cyclohexylamino)ethanesulphonic acid (CHES) or
3-(cyclohexylamino)propanesulphonic acid (CAPS), and their N-halo derivatives can be used separately or in combination in the treatment of related clinical conditions by stimulating myeloperoxidase activity, which in turn stimulates hypochlorous acid production in vivo, which leads inter alia to enhanced leukotriene inactivation.

5 Claims, 1 Drawing Sheet

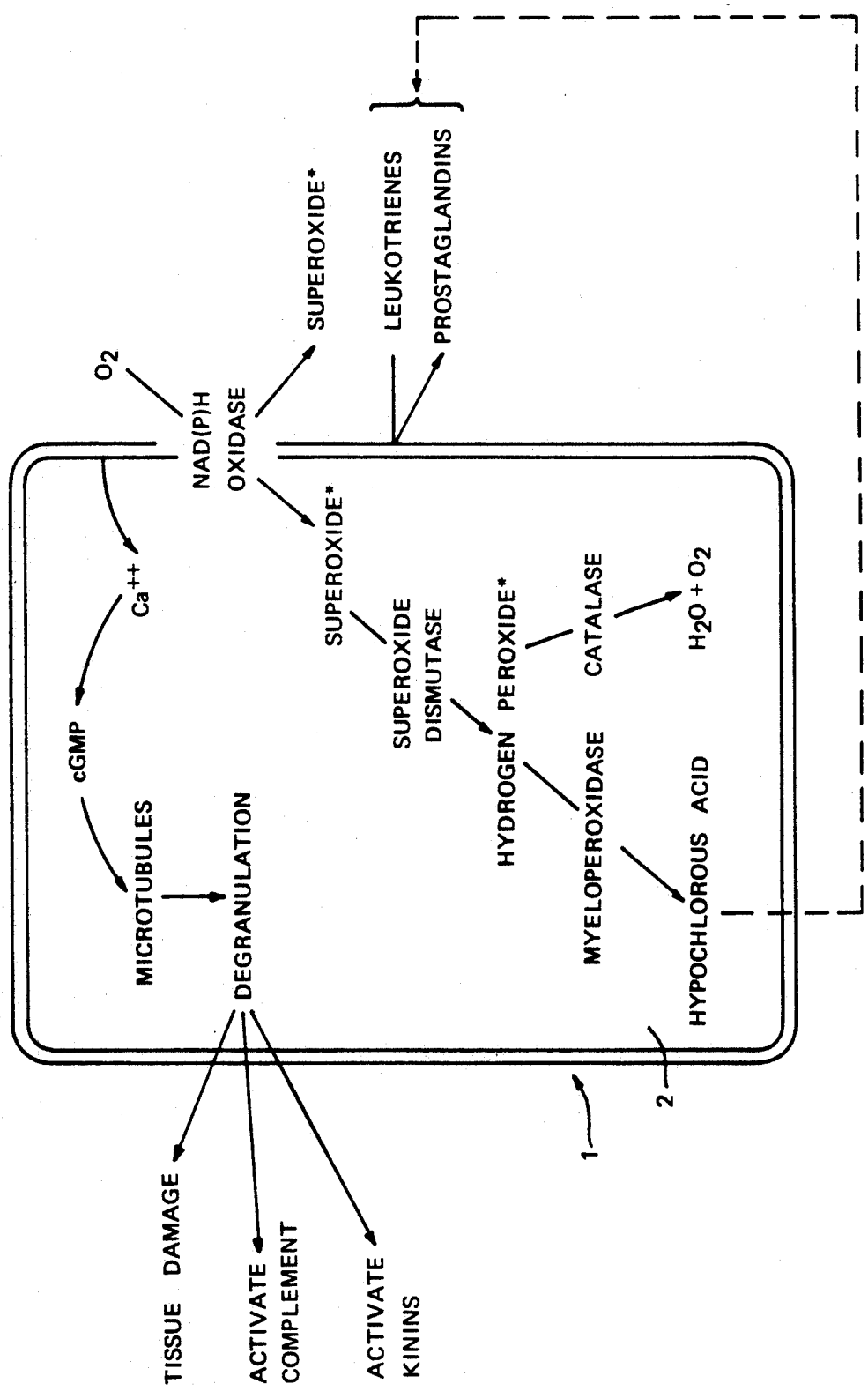

ZWITTERIONIC COMPOUNDS AND THEIR N-HALO DERIVATIVES FOR USE IN THE TREATMENT OF CLINICAL CONDITIONS

FIELD OF THE INVENTION

This invention relates to the use of certain zwitterionic compounds and their N-halo derivatives in the treatment of related clinical conditions.

BACKGROUND AND PRIOR ART

Prostaglandins and leukotrienes are products of arachidonic acid metabolism via the cyclooxygenase pathway and the lipoxygenase pathway, respectively. Leukotriene $B_4$ is one of the most potent naturally occurring mediators of inflammation and is a potent chemotactic and chemokinetic agent for leukocytes. Leukotriene $B_4$ causes in vitro leukocyte accumulation, modulates pain responses and causes changes in vascular permeability. The peptido-lipid conjugates leukotriene $C_4$, $D_4$ and $E_4$ play a lesser role as mediators of inflammation and collectively account for the biological activity known as "slow reacting substance of anaphylaxis". Leukotrienes $C_4$, $D_4$ and $E_4$ are potent smooth muscle contractile agents and are, therefore, believed to be important mediators of asthma and other hypersensitivity reactions. Prostaglandins on the other hand are not causative agents of inflammation, but rather synergise with other inflammatory mediators such as histamine and bradykinin in the production of oedema and pain.

The causes of all inflammatory diseases are unknown and there are no known cures. The aetiology of each condition is often genetically-related, and is usually precipitated by environmental factors. In all inflammatory diseases there is an infiltration of inflammatory cells into the affected areas which leads to a release of mediators of the inflammatory process and concomitant damage to surrounding tissue.

Treatment of inflammatory diseases is normally based on the use of steroidal and non-steroidal anti-inflammatory drugs (NSAIDs). Steroidal drugs include the corticosteroids, for example, cortisol, prednisone, prednisolone, etc. The NSAIDs include the salicylates (e.g. aspirin), pyrazolon derivatives (e.g. phenylbutazone), para-aminophenol derivatives (e.g. phenacetin and acetaminophen), fenamates (e.g. mefenamic acid and flufenamic acid), propionic acid derivatives (e.g. ibuprofen, naproxen, fenoprofen, flurbiprofen and ketoprofen), indomethacin and tolmetin. Both classes of drugs act on arachidonic acid metabolism by inhibiting reactions in the pathways leading to the formation of prostaglandins and leukotrienes. All of the aforementioned drugs have attendant undesirable side-effects with prolonged use and in recent times some NSAIDs have been contra-indicated in certain inflammatory diseases (Rampton, D. S. and Hawkey, C. J. Gut (1984) 25, 1399).

NSAIDs have been reported to inhibit both the cyclooxygenase pathway and the lipoxygenase pathway. In particular, they appear to inhibit formation of 11- and 15-hydroxyeicosatetraenoic acid (HETE). Many cyclooxygenase and lipoxygenase pathway inhibitors are currently being investigated with a view to their being used in therapy.

Benoxaprofen, an NSAID which specifically inhibits 5-lipoxygenase, in addition to cyclooxygenase, was found to markedly improve the inflammatory skin disease psoriasis. However, benoxaprofen was found to produce adverse side effects and its use in such treatment was discontinued. The search is on-going for effective and potent anti-leukotriene agents for use against inflammatory disease by inhibition of the production of the highly potent products of the 5-, 11- and 15-lipoxygenase systems.

Taurine (2-aminoethanesulphonic acid) is found in blood plasma, urine, breast milk, saliva, cerebrospinal fluid, sweat, platelets, leukocytes, muscle, brain, skin and liver. Free taurine is found in millimolar concentrations, especially in tissues that are excitable, rich in membranes and generate reactive oxidants. The function of taurine is not known but because it is abundant where reduced oxygen molecules are generated, and where other toxic substances such as bile salts, retinoids and xenobiotics are found, it is believed that its function is related to attenuation of toxic compounds. Three metabolites of taurine have now been identified viz isethionic acid (2-hydroxyethanesulphonic acid, taurocyamine (guanidotaurine) and taurocholic acid.

Taurine has been tested as an adjunct treatment of hypercholesterolemia and in cardiovascular disorders. Taurine at 1 g per day for seven days reduced or prevented alcohol-withdrawal symptoms (Ikeda, H. Lancet (1977), 2, 509).

French Patent Publication FR-A-7241 describes pharmaceutical compositions for the treatment of arterial disease, comprising taurine and derivatives thereof.

Pharmaceutical compositions for the treatment of psoriasis and comprising at least one zwitterionic aminosulphonic acid (ZASA) compound having a pKa value at 20° C. in the range 6.0–8.3 are the subject of U.S. Pat. No. 4,544,656, hereby incorporated by reference. The zwitterionic compounds include inter alia N-2-hydroxyethylpiperazine-N'-ethanesulphonic acid (HEPES). In U.S. Pat. No. 4,544,656 the anti-psoriatic effect of the ZASAs is attributed to the suppression of neutrophils. This has now been shown to be incorrect as hereinafter described. A variety of drug types are conventionally employed in the treatment of psoriasis due to the different aspects of the disease. Such drugs include anti-inflammatory drugs, anti-proliferative or cytostatic drugs and in severe cases cytotoxic drugs such as methotrexate.

U.S. Pat. No. 4,753,942, hereby incorporated by reference describes the use of the ZASAs specified in U.S. Pat. No. 4,544,656, for the topical treatment of arthritis and/or rheumatism in human patients. As demonstrated hereinafter in Example 7 skin penetration due to percutaneous absorption was not observed following topical administration of HEPES. To alleviate the symptoms of arthritis and rheumatism it would be necessary for the ZASAs to be absorbed percutaneously.

SUMMARY OF THE INVENTION

The present invention provides a method of stimulating myeloperoxidase activity in a patient in need of such stimulation, which comprises administering to said patient as active agent an effective amount of a zwitterionic compound selected from:
taurine (2-aminoethanesulphonic acid),
2(N-morpholino)ethanesulphonic acid (MES),
N-(2-acetamido)iminodiacetic acid (ADA),
piperazine-N,N'bis(2-ethanesulphonic acid (PIPES),
N-(2-acetamido)-2-aminoethanesulphonic acid (ACES),
N,N-bis(2-hydroxyethyl)-2-aminoethanesulphonic acid (BES), 3-(N-morpholino)propanesulphonic (MOPS),
N-N[tris(hydroxymethyl)-methyl]-2-aminoethanesulphonic acid (TES),
N-2-hydroxyethylpiperazine-N'-2-ethanesulphonic acid (HEPES),
N-2-hydroxyethylpiperazine-N'3-propanesulphonic acid ((H)EPPS),
2-(cyclohexylamino)ethanesulphonic acid (CHES) or 3-(cyclohexylamino)propanesulphonic acid (CAPS), and/or an N-halo derivative thereof.

BRIEF DESCRIPTION OF THE FIGURE

The accompanying Figure is a schematic representation of the sequence of events in a neutrophil following an inflammatory stimulus.

DETAILED DESCRIPTION OF PREFERRED EMBODIMENTS

It has now been found that the aforementioned zwitterionic compounds and the N-halo derivatives thereof act as stimulators of the enzyme myeloperoxidase and as leukotriene inactivators as hereinafter described.

By virtue of their ability to inactivate leukotrienes, said zwitterionic compounds and N-halo derivitives thereof can be used in the treatment of inflammatory conditions or diseases, more especially inflammatory conditions or diseases that are progressive and result from autoimmunity.

In one aspect, the invention provides use of said zwitterionic compounds and/or the N-halo derivatives thereof for the treatment of chronic inflammatory conditions or diseases and the active agent is caused to enter the systemic circulation.

In another aspect, the invention provides use of taurine and/or an N-halo derivative of any zwitterionic compound as hereinbefore specified for the treatment of chronic inflammatory conditions or diseases. Thus in this aspect of the invention there is embraced topical administration of such compounds.

Chronic inflammatory diseases include rheumatoid arthritis and other inflammatory joint diseases such as ankylosing spondylitis and psoriatic arthritis, inflammatory skin diseases (psoriasis, eczema and dermatitis herpetiformis), chronic inflammatory bowel disease (Crohn's disease and ulcerative colitis), inflammatory liver disease (chronic active hepatitis and alcoholic hepatitis) and sarcoidosis of the lung.

The zwitterionic compounds and the N-halo derivatives thereof hereinbefore specified hereinafter referred to collectively as zwitterionic compounds except where the context requires otherwise also have other activities in vivo and further uses in therapy as hereinafter specified by virtue of their ability to stimulate the activity of myeloperoxidase. These further activities will be illustrated by reference to the accompanying Figure.

At the cellular level the sequence of events involved in an inflammatory reaction are as follows:- Particulate stimuli (e.g. bacteria) first become coated with complement or antibodies, whereas soluble stimuli (e.g. chemotactic peptides or calcium ionophores) act directly on leukocytes, for example, the neutrophils (1) and monocytes. The coated particles or soluble stimuli engage surface receptors on the cell which cause conformational changes leading to stimulation of the "respiratory burst" and activation of phospholipase. These will be dealt with separately, although both happen simultaneously.

In inflammatory diseases, the inflammatory process is activated in the absence of an apparent pathogenic insult. It is postulated that in many chronic inflammatory conditions that complement binds to the neutrophil surface receptors resulting in a perpetuation of the inflammatory reaction through the cyclical sequence of events depicted in the accompanying Figure, since no known pathogen is involved in such inflammatory conditions.

1. Respiratory Burst

As depicted in the Figure, molecular oxygen is converted to superoxide by NAD(P)H oxidase and is then dismutated to hydrogen peroxide by superoxide dismutase (SOD). This is toxic to the cell and is converted to water and oxygen in the cytosol by catalase. The myeloperoxidase (MPO) system can also convert hydrogen peroxide to hypochlorous acid (in the presence of chloride). Hypochlorous acid thus produced can convert leukotrienes $C_4$, $D_4$ and $E_4$ to inactive metabolites.

Hypochlorous acid inactivates leukotriene $B_4$ by oxidative cleavage and/or halogenation. The stimulated cell releases calcium into the cytoplasm (2) which by a series of events leads to release of other inflammatory mediators from the cell (e.g. neutral proteinases). These cause tissue damage and activate the complement system, (factors which can stimulate more cells). Leukotriene $B_4$ and complement can cause more cells to enter the area of inflammation. Neutral proteinases can also activate the kinin system, which causes vasodilation and hence mobilisation of more cells. Superoxide can cause tissue damage directly, and can activate leukotriene production.

2. Production of Leukotrienes and Prostaglandins

The activation of phospholipase by calcium leads to release of arachidonic acid (which is stored in the membranes of all cells). The free arachidonic acid can then proceed via the lipoxygenase pathway to produce leukotrienes or by the cyclooxygenase pathway to produce prostaglandins. Prostaglandin $E_2$ is a major cyclooxygenase metabolite and this has the capacity to stimulate cyclic AMP formation leading to depression of the process which leads to release of inflammatory enzymes. Prostaglandin $E_2$ also depresses the action of leukotriene $B_4$ and thus limits the inflammatory process. Leukotriene $B_4$ can also stimulate release of inflammatory enzymes from the cell at the site of inflammation. Since leukotrienes are inactivated by hypochlorous acid, the inflammatory process is self-limiting i.e. by its own products.

The zwitterionic compounds hereinbefore specified stimulate MPO by reacting with hypochlorous acid. It is proposed that formation of the corresponding N-halo derivatives prevents feedback inhibition of hypochlorous acid on MPO leading to enhanced enzyme activity and increased metabolism of reactive oxidants as hereinafter demonstrated.

As used herein the term reactive oxidant embraces hydrogen peroxide and even hypochlorous acid.

The zwitterionic compounds can be used in the treatment of patients with hereditary MPO deficiency, a genetic disorder in which MPO is deficient in neutrophils and monocytes leading to susceptibility to infection.

By virtue of their action on MPO, the zwitterionic compounds cause removal of reactive oxidants by enhancing the metabolism thereof.

Thus the invention provides a method of using such zwitterionic compounds in the removal of reactive oxidants by enhancing the metabolism thereof. Accordingly it is proposed that such zwitterionic compounds can be used in cancer therapy and as general anti-neoplastic agents.

As indicated above, the zwitterionic compounds also indirectly stimulate production of hypochlorous acid.

It is well known that hypochlorous acid has strong anti-bacterial properties, and its production during the respiratory burst hereinabove described plays an important role in killing bacteria which are ingested by inflammatory cells in the event of infection. Thus the enhancement of MPO in vivo by the compounds hereinbefore specified in accordance with the invention has a bactericidal effect due to the promotion of hypochlorous acid production.

Accordingly, in a further aspect of the invention there is provided use of a zwitterionic compound as hereinbefore specified as an antibacterial agent.

The zwitterionic compounds hereinabove specified were first described by Good, N. E., et al. Biochemistry (1966) 5, 467, hereby incorporated by reference.

Preferred zwitterionic compounds for use in accordance with the invention are HEPES and taurine, subject to the above limitation.

Preferred N-halo derivatives of zwitterionic compounds for use in accordance with the invention are HEPES halamine and taurine halamine. Preferred N-halo derivatives are the N-chloro and N-iodo derivatives.

The invention also provides a method wherein a zwitterionic compound as hereinbefore defined is administered simultaneously, separately or sequentially with an N-halo derivative of a zwitterionic compound as hereinbefore defined.

The invention further provides a pharmaceutical composition comprising a combination of a zwitterionic compound as hereinbefore specified and an N-halo derivative of such a zwitterionic compound.

It will be appreciated that a combination of a zwitterionic compound and an N-halo derivative of such a zwitterionic compound will potentiate the effect of either compound used alone. Indeed, such combinations have been found to produce a synergistic effect in in vitro studies as hereinafter demonstrated.

The N-halo derivatives of the zwitterionic compounds as hereinbefore defined can be prepared by reacting the corresponding zwitterionic compounds with a hypohalous acid or a salt thereof.

When a salt of a hypohalous acid is used, the salt is preferably an alkali metal salt, more especially sodium.

Medicaments for use in accordance with the invention preferably contain the active ingredient in an amount of 0.05–5% by weight.

Medicaments for use in accordance with the invention may be administered locally or systemically depending on the proposed use of the active ingredient in accordance with the invention. By systemic administration is meant any mode or route of administration which results in effective levels of active ingredient appearing in the blood or at a site remote from the site of administration of said active ingredient.

The medicaments for systemic administration according to the invention may be formulated for enteral, parenteral or topical administration. Indeed, all three types of medicaments can be used simultaneously to achieve systemic administration of the active ingredient.

Suitable formulations for oral administration include capsules (hard or soft gelatine capsules) dragees, pills, tablets, including coated tablets, elixirs, suspensions and syrups, including controlled release forms thereof.

Suitable preparations for parenteral administration include injectable solutions and perfusion solutions. The injectable solutions may include intramuscular, intravenous and subcutaneous injectable solutions.

Medicaments for use according to the invention also include rectal suppositories and vaginal pessaries. A particularly suitable formulation for the treatment of inflammatory bowel disease is an enema.

Suitable formulations for topical administration include creams, gels, jellies, mucilages, pastes and ointments. The active ingredient may also be formulated for transdermal administration.

The invention will be further illustrated by the following Examples. It will be understood that the specification and examples are illustrative but not limitative of the present invention and that other embodiments within the spirit and scope of the invention will suggest themselves to those skilled in the art.

EXAMPLE 1

Taurine chloramine is prepared as follows: Taurine (500 mg) is dissolved in water (50 ml). Sodium hypochlorite (approx. 1N in 0.1N) is diluted in 1 in 100 with water. 50 ml of the taurine solution is reacted with 50 ml of the diluted sodium hypochlorite. The taurine chloramine thereby obtained is freeze dried to remove residual hypochlorite.

EXAMPLE 2

Tablets having the following composition are prepared:

| | |
|---|---|
| HEPES | 4 mg |
| HEPES Chloramine | 4 mg |
| Lactose | 50 mg |
| Avicel | 40 mg |
| Magnesium stearate | 6 mg | by mixing the active ingredients with the other constituents and compressing the product to form the tablets.

EXAMPLE 3

Capsules are prepared having the following composition:

| | |
|---|---|
| HEPES | 3 mg |
| HEPES Chloramine | 3 mg |
| Lactose | 90 mg |
| Magnesium stearate | 7 mg | by intimately mixing the above ingredients and pouring the mixture into hard gelatine capsules.

EXAMPLE 4

A sterile aqueous solution appropriate for parenteral use, having the following composition, is prepared:

| | |
|---|---|
| HEPES | 4 mg |

-continued

| | |
|---|---|
| HEPES Chloramine | 4 mg |
| Water for injectables | 2 ml | the solution is filled into sterile ampoules.

EXAMPLE 5

Suppositories are prepared, having the following composition:

| | |
|---|---|
| HEPES | 5 mg |
| HEPES Chloramine | 5 mg |
| Lactose | 300 mg |
| Witespol W (Witespol ® is a Trade Mark) 45 g.s.p. | 1.5 g |

The active ingredient is mixed with the lactose and then uniformly suspended in the Witespol ® W 45 and heated to a molten mass in conventional manner. The suspension is poured into cooled moulds to form suppositories weighing 1.5 g.

EXAMPLE 6

A vanishing cream is made up of the following:

| | % w/w |
|---|---|
| Oil Phase | |
| Liquid paraffin | 30 |
| Span ® 65 (Span is a Trade Mark) | 1 |
| Cetosteryl alcohol | 5 |
| Propyl parabens | 0.1 |
| Aqueous Phase | |
| Carbopol ® 934 gel (1.0%) (Carbopol is a Trade Mark) | 36.5 |
| Tween ® 85 (Tween is a Trade Mark | 2 |
| Glycerol | 20 |
| Taurine | 5 |
| Methyl parabens | 0.4 |

A 1% Carbopol ® 934 gel is prepared by dispersing 2 g of Carbopol ® in 150 g water. The pH is adjusted to 7 with 1N NaOH. The gel is then brought to 200 g with water. The oil phase is heated to 70° C. and added to the water phase in a mortar and sheared for 30 min. with gradual reduction of temperature.

EXAMPLE 7

Investigation of skin penetration and percutaneous absorption of HEPES

The skin penetration and percutaneous absorption of radioactivity following topical administration of a single does of $^{14}C$-HEPES (approximately 100 mg 5% cream containing 70 uCi $^{14}C$) was investigated in two groups of six healthy male volunteers. The dose was applied to intact skin in one group and to skin stripped 10 times with scotch tape in the second group. The unabsorbed material was removed after 12 hours and the area of application was stripped 10 times in order to determine skin penetration. Blood, urine and faeces samples were collected up to 120 hours after dose application for assessment of total radioactivity.

No radioactivity was detected in any of the plasma or faecal samples, with the exception of one subject in the "stripped skin" groups for whom 0.11% of the applied dose was detected in the 48–72 hour faecal sample.

Mean urinary excretion of radioactivity in the "intact" and "stripped" groups respectively was 0.07+0.08 (S.D.) and 0.20±0.22 (S.D.) percent of the applied dose.

Isolated abnormalities in biochemistry, haematology and urinalysis screens were not considered to be related to $^{14}C$-HEPES administration.

In summary, a single topical dose of $^{14}C$-HEPES was well tolerated in this study in both "intact" and "stripped" skin groups and there was negligible absorption of radioactivity.

IN VITRO STUDIES

Mechanism of Action

The mechanism of action of the aforementioned compounds acting as NSAIDs has been elucidated using taurine and HEPES as the ingredient except where otherwise stated, and psoriasis and other inflammatory skin diseases as a model for inflammatory disease due to the necessity to obtain permission from the regulatory authority before undertaking trials involving internal administration.

Patients were selected with mild to moderate plaque-type psoriasis on the basis of clinical and histological evidence of disease. Normal volunteers were selected from laboratory personnel without personal or family history of inflammatory disease. Disease control groups included: a) patients with eczema, acne and dermatitis herpetiformis; and b) patients with Crohn's disease and ulcerative colitis.

Blood samples from each subject were drawn into sodium heparin Vacutainers ® (Vacutainer is a Trade Mark). The inflammatory cells (neutrophils) were isolated by dextran sedimentation and FICOLL-PAQUE ® (FICOLL-PLAQUE is a Trade Mark) gradient centrifugation. Viability and purity were assessed by fluorescence microscopy, using ethidium bromide and acridine orange staining.

In all studies, the parameters of interest were measured after preincubation in the absence or presence of 40 mM taurine, pH 8.0 or 10 mM HEPES or other zwitterions, pH 6.0, for 1 min. at 37° C. It was demonstrated that the preincubation step was necessary for stimulation of MPO activity. Preliminary studies demonstrated that taurine or HEPES did not bind to the enzyme to produce a stimulatory effect. As indicated above the stimulation of MPO was found to be due to reaction of hypochlorous acid with taurine or HEPES, which prevents feedback inhibition of hypochlorous acid on MPO and, therefore, allows more of the enzyme to remain in its active state.

Determination of Chemiluminescence

Chemiluminescence activity of the peripheral blood neutrophils was tested using the method of Bloomfield, F. J. and Young, M. M. (Inflammation, (1982) 6, 257, hereby incorporated by reference), using calcium ionophore (2μ Molar) as stimulant instead of opsonized zymosan. Chemiluminescence is a measure of the production of reactive oxidants by neutrophils in response to an inflammatory stimulus. It was observed that there was significant reduction in chemiluminescence activity by neutrophils in the taurine-treated and HEPES-treated cells compared to control cells in all groups. The results are given in Table 1.

TABLE 1

Chemiluminesence production by neutrophils preincubated in 10 mM HEPES or 40 mM taurine expressed as percentage activity of control (without zwitterion).

| | HEPES | | Taurine | |
|---|---|---|---|---|
| | n | Mean S.E.M. | n | Mean S.E.M. |
| Psoriasis | (31) | 26.9 ± 3.25 | (10) | 15.5 ± 2.10 |
| Normal | (29) | 28.8 ± 4.24 | (8) | 12.7 ± 1.77 |
| D.C.*(a) | (22) | 28.8 ± 3.84 | (20) | 20.3 ± 1.85 |
| D.C.*(b) | (37) | 25.4 ± 6.4 | (17) | 30.5 ± 8.6 |

D.C.* = Disease Controls as hereinbefore specified

In the experiments carried out, it was observed that HEPES and taurine had significantly reduced the observed response, either by inhibition of the inflammatory response (the respiratory burst) or by removal of reactive oxidants by a process hitherto unknown.

To test these hypotheses, a number of experiments were carried out.

Investigation of degranulation

Stimulation of the inflammatory process in neutrophils, not only activates the respiratory burst, but as a consequence, is also associated with release of lysosomal enzymes from the cells in a process called degranulation. Degranulation of lysosomal enzymes was stimulated in neutrophils from each group of subjects, using calcium ionophore as inflammatory stimulant. The results are given in Table 2.

TABLE 2

Degranulation by neutrophils preincubated in 10 mM HEPES expressed as percentage activity of control (without HEPES).

| | n | Mean | | S.E.M. |
|---|---|---|---|---|
| Psoriasis | (10) | 104 | ± | 15.7 |
| Normal | (28) | 104 | ± | 15.6 |
| D.C.*(a) | (6) | 87.2 | ± | 12.1 |

D.C.* = Disease Controls as hereinbefore specified

It was observed that there was no difference in degranulation by neutrophils preincubated with HEPES compared to control cells preincubated without HEPES. It was also observed that there was no significant difference in degranulation by neutrophils preincubated with taurine compared to control cells (data not shown). This suggests that HEPES or taurine does not cause suppression of neutrophils. It appeared, therefore, that the reduced chemiluminescence observed in the presence of HEPES or taurine (see Table 1) could have been due to removal of reactive oxidants produced during the respiratory burst.

Determination of Catalase and Myeloperoxidase

To test the hypothesis of increased removal of reactive oxidants by the action of HEPES or taurine, two enzymes involved in their removal were measured in the neutrophils after preincubation with HEPES or taurine. It was observed that, whereas HEPES or taurine had no effect on catalase activity (data not shown), MPO activity was significantly enhanced in all subjects in the presence of 10 mM HEPES or 40 mM taurine. The results are given in Table 3.

TABLE 3

Myeloperoxidase activity of neutrophils preincubated in 10 mM HEPES or 40 mM taurine expressed as percentage activity of control (without zwitterion).

| | HEPES | | Taurine | |
|---|---|---|---|---|
| | n | Mean S.E.M. | n | Mean S.E.M. |
| Psoriasis | (44) | 247 ± 30.1 | (20) | 591 ± 61.8 |
| Normal | (24) | 228 ± 25.4 | (19) | 564 ± 38.3 |
| D.C.*(a) | (14) | 198 ± 17.1 | (9) | 473 ± 33.7 |
| D.C.*(b) | (20) | 211 ± 56.4 | (12) | 485 ± 49.2 |

D.C.* = Disease Controls as hereinbefore specified

These results suggested that as a consequence of enhanced myeloperoxidase activity the reactive oxidant, hydrogen peroxide, was being removed more rapidly and converted to hypochlorous acid (see Figure). These observations accounted for the reduced chemiluminescence activity observed in the presence of HEPES (see Table 1). It will be observed that myeloperoxidase is significantly more active in the presence of taurine than in the presence of HEPES.

Production of hypochlorous acid

The data obtained suggested that there was increased metabolism of hydrogen peroxide through the myeloperoxidase-halide system in the presence of HEPES. Increased production of hypochlorous acid by chlorination of hydrogen peroxide was also demonstrated in the presence of HEPES or taurine. The results are given in Table 4.

TABLE 4

Hypochlorous acid production by neutrophils preincubated in 10 mM HEPES or 40 mM taurine expressed as percentage activity of control (without zwitterion).

| | HEPES | | Taurine | |
|---|---|---|---|---|
| | n | Mean S.E.M. | n | Mean S.E.M. |
| Psoriasis | (25) | 193 ± 10.7 | (18) | 167 ± 34.7 |
| Normal | (15) | 211 ± 12.5 | (15) | 152 ± 14.1 |
| D.C.*(a) | (20) | 152 ± 8.3 | (20) | 142 ± 32.1 |

D.C.* = Disease Controls as hereinbefore specified

It is known that hypochlorous acid plays a central role in the modulation of the inflammatory process. Taurine can form a chloramine in the presence of hypochlorous acid. Reaction of hypochlorous acid with HEPES or taurine would prevent feedback inhibition of hypochlorous acid on MPO and this would account for the enhanced enzyme activity demonstrated in the presence of HEPES or taurine (See Table 3).

Therefore, stimulation of MPO by HEPES and other zwitterions not only leads to a reduction of toxic oxygen radicals (as shown by chemiluminescence) but also leads to increased production of hypochlorous acid and chloramines which causes breakdown of leukotriene $B_4$.

Production of N-halo derivatives of zwitterionic compounds (halamines).

In the presence of hypochlorous the aforementioned zwitterionic compounds form stable halamines as shown in the scheme hereunder.

$$HOCl + H_2N-R \rightarrow ClNH-RH + H_2O$$

where R is the remainder of the zwitterionic compound.

In a further experiment such halamine formation was demonstrated by the method of Weiss et al (J. Clin. Invest. (1982) 70, 598, hereby incorporated by reference).

Using spectrophotometric procedures the zwitterionic compounds show no absorption between 210 and 280 nm in the ultraviolet range.

Hypochlorous acid absorbs maximally at 290 nm. The halamines formed by the zwitterionic compounds absorb maximally at 250 nm and this was demonstrated by incubating the zwitterionic compounds with hypochlorous acid.

It is proposed that formation of chloramines prevents feedback inhibition of hypochlorous acid on MPO leading to enhanced enzyme activity (See Table 3) and increased metabolism of reactive oxidants resulting in reduced chemiluminscence (See Table 1) as indicated above.

Inactivation of Leukotrienes

It is known that the MPO-halide system plays an important role in the breakdown of active leukotrienes ($C_4$, $D_4$ and $E_4$) to inactive chiral sulphoxides and diastereoisomers of 6-trans-leukotriene $B_4$ (Lee, V. Y., et al. Clin. Sci. (1982) 63, 219, hereby incorporated by reference). This effect is due to the action of hypochlorous acid produced from hydrogen peroxide in the cells, by the MPO-halide system, on the active leukotrienes.

Leukotriene $B_4$ has also been demonstrated to be inactivated by the MPO-halide system, possibly by oxidative cleavage or halogenation (Henderson W. R., Toig, A. and Klebanoff, S. J. Immunol. (1982) 128, 2609, hereby incorporated by reference) and such inactivation of leukotriene $B_4$ would have potent anti-inflammatory action. It was therefore proposed to test the hypothesis that HEPES could inactivate leukotriene $B_4$ by indirect stimulation of MPO leading to increased production of hypochlorous acid from cellular hydrogen peroxide. It was initially demonstrated that hypochlorous acid, taurine chloramine or HEPES-chloramine cause degradation of standard leukotriene $B_4$, as measured by radioimmunoassay (data not shown). Table 5 demonstrates that preincubation of cells with 10 mM HEPES or 40 mM taurine significantly reduced leukotriene $B_4$ in the supernatants of stimulated neutrophils of all groups. This effect was also demonstrated in monocytes, which also have the capacity to produce large amounts of leukotriene $B_4$ (data not shown). These results show that HEPES and taurine can indirectly cause inactivation of leukotrienes, particularly leukotriene $B_4$ and can be used therefore in all conditions characterised by raised leukotriene levels, including chronic inflammatory conditions.

In further studies, we observed that normal cells preincubated with HEPES in the presence of 1 mM potassium iodide showed no measurable leukotriene $B_4$ in the supernatants demonstrating an increased breakdown of active leukotriene $B_4$ by hypoiodous acid (Table 5). These data support the concept that other halide cofactors may be more effective than chloride in this system.

For the methodology used in the in vitro studies hereinafter described reference should be made to McLoughlin, D. M. et al. Biochem. Soc. Trans. (1991) 19:73-78 hereby incorporated by reference, except where otherwise stated.

The chemicals for the invention are readily available from chemical laboratory suppliers e.g. Sigma Chemical Company, St. Louis, Mo.

TABLE 5

Leukotriene $B_4$ production by neutrophils preincubated in 10 mM HEPES or 40 mM taurine expressed as percentage activity of control (without zwitterion).

| | HEPES | | Taurine | |
|---|---|---|---|---|
| | n | Mean S.E.M. | n | Mean S.E.M. |
| Psoriasis | (24) | 22.4 ± 6.62 | (16) | 66.5 ± 10.94 |
| Normal | (13) | 55.8 ± 8.90 | (16) | 64.8 ± 8.30 |
| D.C.*(a) | (13) | 24.9 ± 8.99 | (6) | 73.3 ± 9.95 |
| D.C.*(b) | (28) | 16.7 ± 6.42 | (9) | 78.0 ± 8.60 |
| Normal + iodide | (4) | 0 ± 0 | — | — |

D.C.* = Disease Controls as hereinbefore specified

Since inflammatory diseases are increasingly being associated with enhanced production of leukotrienes (Ford-Hutchinson, A. W., J. Allergy Clin. Immunol. (1984) 74, 437, hereby incorporated by reference), the results indicated in Table 5 demonstrate that HEPES or taurine can be used to inactivate inflammatory leukotrienes and lead to an improvement of inflammatory diseases.

The other zwitterionic compounds have been investigated and show similar effects on chemiluminescence and MPO activity. Table 6 is a summary of the effects of zwitterions on MPO and chemiluminescence activity. The same procedures were used as in the case of the MPO and chemiluminescence estimations for HEPES or taurine.

TABLE 6

Myeloperoxidase and chemiluminescence activity of normal neutrophils preincubated in 10 mM zwitterionic compound expressed as percentage activity of control (without zwitterion).

| | Myeloperoxidase | | Chemiluminescence | |
|---|---|---|---|---|
| Zwitterion | n | Mean S.E.M. | n | Mean S.E.M. |
| MES | (6) | 264 ± 15.9 | (6) | 3.15 ± 0.67 |
| ADA | (4) | 214 ± 32.3 | (6) | 1.45 ± 0.27 |
| PIPES | (6) | 199 ± 23.1 | (6) | 4.08 ± 0.97 |
| ACE | (4) | 166 ± 18.2 | (6) | 12.90 ± 2.75 |
| BES | (6) | 138 ± 14.1 | (6) | 4.95 ± 0.93 |
| MOPS | (6) | 134 ± 13.4 | (6) | 7.27 ± 1.53 |
| TES | (6) | 129 ± 20.1 | (6) | 15.60 ± 2.41 |
| (H)EPPS | (4) | 348 ± 15.1 | (6) | 50.90 ± 7.38 |
| CHES | (4) | 120 ± 4.8 | (6) | 68.40 ± 6.36 |
| CAPS | (4) | 115 ± 3.6 | (6) | 87.90 ± 8.87 |

No overall correlation was observed between myeloperoxidase enhancement and chemiluminescence activity. However, it was demonstrated that (H)EPPS, MES, PIPES and ACES had a marked effect on MPO activity with BES, MOPS and TES having a lesser effect on MPO stimulation. CHES and CAPS had little effect. Chemiluminesence activity was markedly reduced in the presence of all zwitterions except (H)EPPS, CHES, and CAPS.

IN VIVO STUDIES

The effect of taurine injected intracerebroventricularly (i.c.v.) or subcutaneously (s.c.) and HEPES infected intraperitoneally (i.p.) on the modulation of carrageenan-induced paw inflammation in rats was investigated. In addition, the effect of taurine on reactive oxidant (RO) production by isolated rat peripheral blood mononuclear cells (PBMC) was also studied using chemiluminescence.

Intracerebroventricular injection of taurine

The studies were conducted on inbred Wistar strain albino rats (120–180 g) of either sex. The rats were housed in colony cages at an ambient temperature of 25°±2° C. and fed on standard pellet chow. The rats were anaesthetized using pentobarbitone sodium, their hind paws were marked and the volume measured. Stock taurine solutions were prepared in 0.9% NaCl and 10 μl was injected into the right lateral ventricle. The control animals were injected with 10 μl of 0.9% saline solution. 30 min. after the taurine injection, paw oedema was induced by carrageenan (100 μl of 1% suspension in 0.9% saline), injected below the plantar aponeurosis of the hind paws. One hour following the carrageenan injection the hind paw volume was measured again. A 5 ml blood sample was taken from each animal into sodium heparin Vacutainers. Chemiluminescence activity was assayed in the PBMC isolated from each animal.

Subcutaneous injection of taurine and intraperitoneal injection of HEPES

These studies were also conducted on inbred Wistar strain albino rats (120–180 g) of either sex. The rats were anaesthetized using pentobarbitone sodium prior to marking each hind paw and measuring paw volume. 10 μl of stock taurine or HEPES solution was made up to 0.5 ml using 0.9% NaCl and injected subcutaneously (taurine) or intraperitoneally (HEPES) into the experimental animals. The control animals received 0.5 ml of 0.9% NaCl subcutaneously. 30 min after the injections were administered, paw oedema was induced using carrageenan. One hour following carrageenan administration the hind paw volume was measured. A 5 ml blood sample was taken from each animal into sodium heparin Vacutainers and used for chemiluminescence measurement.

Isolation of PBMC

Whole rat blood (5 ml) was collected into sodium heparin Vacutainers, added 5 ml dextran, mixed thoroughly by inverting several times and allowed to sediment at room temperature for approximately 30 min. The plasma layer was removed and added to an equal volume of 0.9% saline, and centrifuged at 800 g for 5 min. at 20° C. The supernatant was disposed and the pellet retained. Residual erythrocytes were lysed by sequential addition of 3 ml of filtered deionised $H_2O$ and 1 ml 3.6% NaCl. The cells were centrifuged at 800 g for 5 min. and the supernatant discarded. The pellet was resuspended in 5 ml of 0.9% NaCl. This pellet contained the PBMC. The percentage of monocytes in rat PBMC is estimated at 10% of total cells and this was used for further calculations.

The results of i.c.v. injection of taurine (500 μg), on carrageenan-induced paw oedema are summarised in Table 7. Taurine administered centrally produced a dose-related attenuation of paw oedema. The 500 μg dose of taurine produced a 54% reduction in paw oedema, whereas the 50 μg dose of taurine produced a 21% reduction in paw oedema. However, the anti-inflammatory effect was only statistically significant with the 500 μg dose of taurine ($P<0.05$). Table 7 also outlines the results of s.c. administration of taurine (500 μg). There was an 18% reduction in paw oedema but this was not statistically significant. Intraperitoneal injection of HEPES (500 μg) produced a 50% reduction in paw oedema which was statistically significant.

TABLE 7

Effect of i.c.v. and s.c. administered taurine and i.p. administered HEPES on carrageenan induced paw oedema in rats expressed as percentage increase in paw volume.

| | Control | | Experimental | |
|---|---|---|---|---|
| | n | Mean S.E.M. | n | Mean S.E.M. |
| I.C.V. (500 μg taurine) | (4) | 46 ± 8 | (4) | 21 ± 8* |
| I.C.V. (50 μg taurine) | (5) | 38 ± 10 | (5) | 30 ± 4 |
| S.C. (500 μg taurine) | (6) | 33 ± 4 | (6) | 27 ± 2 |
| I.P. (500 μg HEPES) | (4) | 46 ± 5 | (4) | 23 ± 4* |

Significant difference from controls is indicated by *$P < 0.05$.

Table 8 shows the effect of i.c.v. injection of taurine (500 or 50 μg), and s.c. injection of taurine (500 μg) on the chemiluminescence response of isolated PBMC. For both concentrations of i.c.v. injection of taurine there was a statistically significant reduction in chemiluminescence ($P<0.05$). S.c. administration of taurine (500 μg), did not produce a significant reduction in chemiluminescence.

TABLE 8

Effect of i.c.v. and s.c. administered taurine on chemiluminescence activity of isolated PBMC from rats expressed as percentage activity of control (without taurine).

| | n | Mean S.E.M. |
|---|---|---|
| I.C.V. (500 μg) | (3) | 47.3 ± 16.9* |
| I.C.V. (50 μg) | (4) | 42.4 ± 2.3* |
| S.C. (500 μg) | (6) | 101.1 ± 22.1 |

Significant difference from controls is indicated by *$P < 0.05$.

It was found that taurine administered centrally produced a dose-related attenuation of carrageenan-induced paw inflammation. 500 μg of taurine injected i.c.v. produced a 54% reduction in paw oedema, whereas 50 μg of taurine produced a 21% reduction. However, the anti-inflammatory effect was only statistically significant with the 500 μg dose taurine ($P<0.05$). S.c. administration of taurine (500 μg) produced an 18% reduction in paw oedema but it was not statistically significant. For both concentrations of i.c.v. injected taurine there was a statistically significant decrease in chemiluminescence ($P<0.05$). However, administration of taurine subcutaneously (500 μg) did not produce a significant reduction in chemiluminescence.

As stated above the anti-psoriatic effect of the ZASA's is not attributable to the suppression of neutrophils as alleged in U.S. Pat. No. 4,544,656. Rather as demonstrated herein the mechanism of action of HEPES and other zwitterions is related to activation of myeloperoxidase which causes catabolism of leukotriene $B_4$ and as a consequence reduces the inflammatory response.

I claim:

1. A method for treating a chronic progressive inflammatory condition or disease by stimulating myeloperoxidase activity comprising systemically administering to a patient in need thereof an effective amount of taurine and at least one N-halo derivative of a zwitterionic compound selected from the group consisting of:
taurine (2-aminoethanesulphonic acid),
2(N-morpholino)ethanesulphonic acid (MES),
N-(2-acetamido)iminodiacetic acid (ADA),
piperazine-N,N'bis(2-ethanesulphonic acid (PIPES),
N-(2-acetamido)-2-aminoethanesulphonic acid) (ACES),
N,N-bis(2-hydroxylethyl)-2-aminoethanesulphonic acid) (BES), 3-(N-morpholino)propanesulphonic (MOPS),
N,N[tris(hydroxymethyl)-methyl]-2-aminoethanesulphonic acid) (TES),
N,2-hydroxyethylpiperazine-N'-2-ethanesulphonic acid) (HEPES),
N,2-hydroxyethylpiperazine-N'-3-propanesulphonic acid) ((H)EPPS),
2-(cyclohexylamino)ethanesulphonic acid) (CHES), and
3-(cyclohexylamino)propanesulphonic acid) (CAPS), wherein said taurine and said N-halo derivative are administered simultaneously, separately, or sequentially.

2. The method according to claim 1, wherein said N-halo derivative of a zwitterionic compound is an N-halo derivative of HEPES.

3. The method according to claim 1, wherein said N-halo derivative is an N-chloro or N-iodo derivative.

4. Method for treating a chronic, progressive, inflammatory condition or disease comprising administering to a patient in need thereof an effective amount of taurine sufficient to stimulate myeloperoxidase activity.

5. Method of claim 4, further comprising administering an N-halo derivative of a compound selected from the group consisting of
taurine (2-aminoethanesulphonic acid),
2(N-morpholino)ethanesulphonic acid (MES),
N-(2-acetamido)iminodiacetic acid (ADA),
piperazine-N,N'bis(2-ethanesulphonic acid (PIPES),
N-(2-acetamido)-2-aminoethanesulphonic acid) (ACES),
N,N-bis(2-hydroxylethyl)-2-aminoethanesulphonic acid) (BES),
3-(N-morpholino)propanesulphonic (MOPS),
N,N[tris(hydroxymethyl)-methyl]-2-aminoethanesulphonic acid) (TES),
N,2-hydroxyethylpiperazine-N'-2-ethanesulphonic acid) (HEPES),
N,2-hydroxyethylpiperazine-N'-3-propanesulphonic acid) ((H)EPPS),
2-(cyclohexylamino)ethanesulphonic acid) (CHES) and
3-(cyclohexylamino) propanesulphonic acid) (CAPS).

* * * * *